United States Patent

Tsang et al.

[11] Patent Number: 5,769,539
[45] Date of Patent: Jun. 23, 1998

[54] BACKFLUSH SYSTEM FOR A FILTER MEMBRANE LOCATED UPSTREAM OF A HYDROCARBON ANALYZER APPARATUS

[75] Inventors: Charles Tsang, Vancouver; Victoria Shien-fern Ker, Richmond; Adrian H. Wong, Vancouver, all of Canada

[73] Assignee: Phase Technology, Richmond, Canada

[21] Appl. No.: 511,974

[22] Filed: Aug. 7, 1995

[51] Int. Cl.$^6$ .......................... G01N 25/00; B01D 29/00; B01D 41/00
[52] U.S. Cl. .......................... 374/16; 210/636; 374/141; 73/863.24
[58] Field of Search .................. 374/16, 141; 73/863.24; 436/178; 210/636, 321.69

[56] References Cited

U.S. PATENT DOCUMENTS

| | | | |
|---|---|---|---|
| 3,457,787 | 7/1969 | Maatsch et al. | 73/863.24 |
| 3,519,401 | 7/1970 | Hellman | 210/636 |
| 3,733,906 | 5/1973 | Barnhardt et al. | 73/863.24 |
| 3,748,906 | 7/1973 | Manka | 73/863.24 |
| 5,088,833 | 2/1992 | Tsang et al. | 374/17 |
| 5,090,817 | 2/1992 | Ker et al. | 374/24 |
| 5,221,479 | 6/1993 | Etoh et al. | 210/636 |
| 5,393,433 | 2/1995 | Espenan et al. | 210/636 |

FOREIGN PATENT DOCUMENTS

| | | | |
|---|---|---|---|
| 0017581 | 2/1978 | Japan | 210/636 |
| 0102281 | 9/1978 | Japan | 210/636 |
| 0108882 | 9/1978 | Japan | 210/636 |
| 0024006 | 3/1981 | Japan | 210/636 |
| 2126922 | 5/1990 | Japan | 210/636 |
| 1381410 | 1/1975 | United Kingdom | 210/636 |

*Primary Examiner*—Diego F. F. Gutierrez
*Attorney, Agent, or Firm*—Kenneth H. Johnson

[57] ABSTRACT

A hydrocarbon analyzer wherein the filter is backflushed by the liquid sample. The motive force for the backflush is provided by energy stored from the pumping of the liquid sample in a compressible fluid in contact with the sample downstream of the filter. After the sample has been analyzed the pressure on the upstream side of the filter is lowered and the energy in the compressible fluid is released pushing the liquid sample back across the filter providing a backflush.

11 Claims, 1 Drawing Sheet

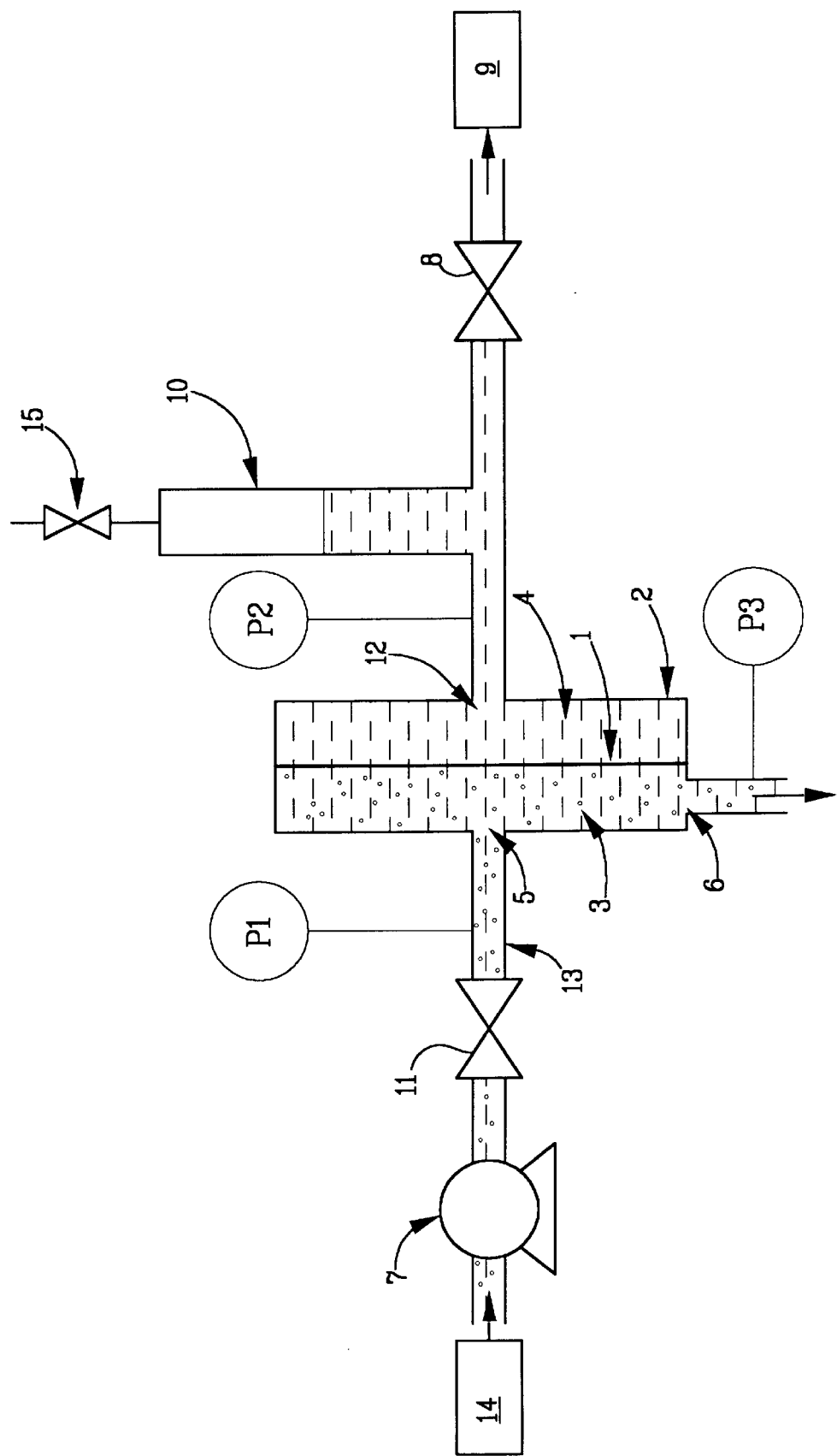

BACKFLUSH SYSTEM FOR A FILTER MEMBRANE LOCATED UPSTREAM OF A HYDROCARBON ANALYZER APPARATUS

FIELD OF INVENTION

This invention provides an improved hydrocarbon analyzer.

BACKGROUND

Hydrocarbon analyzers are used to measure various physical and chemical properties of petroleum products such as cloud point, freeze point, pour point, vapor pressure, octane number and sulfur content. Examples of such analyzers were disclosed in U.S. Pat. Nos. 5,088,833 and 5,090,817. A key part of any on-line freeze point and cloud point analyzer system is sample conditioning. The samples (e.g. hydrocarbons such as diesels and jet fuels) typically contain water, suspended solids and gas bubbles. In order for the analyzer to function properly, these contaminants must be removed from the sample stream. The sample conditioning unit must provide a clean batch of sample to the analyzer at the beginning of each analysis. The sample must also be sufficient in quantity to purge out the previous sample in the analyzer.

In many prior art analyzers, a filter membrane is used to remove contaminants. A filter membrane has a tendency to foul. Accordingly, an invention that will mitigate the problem caused by filter fouling would be a useful addition to the art.

SUMMARY OF INVENTION

The present invention provides an improved hydrocarbon analyzer apparatus having a filter membrane located upstream of the apparatus, wherein the improvement comprises a backflush system for the filter membrane.

In another embodiment, the invention provides an improved hydrocarbon analyzer apparatus wherein the backflush system is characterized by an anticlogging chamber, wherein the anticlogging chamber is located downstream from the filter membrane and wherein the anticlogging chamber contains a compressible fluid.

BRIEF DESCRIPTION OF DRAWING

The FIGURE provides a schematic illustration of the preferred embodiment of an apparatus according to the invention.

DETAILED DESCRIPTION

This is a method to keep a filter from being plugged with solids by using a compressed fluid (air or other gases) as a motive force to backflush the filter. A chamber filled with a compressible fluid such as an inert gas is installed downstream of a filter as a side branch from the main filtrate (filtered product) stream.

As filtration proceeds, a solution carrying suspended particles is forced through the filter by a forward motive force. This forward motive force can be provided by a pressure source such as a pump. The particles in the solution are retained by the filter; therefore, the filtrate is free of the particles. However, the build up of particles on the filter causes a decay in filtration efficiency as the pores in the filter are blocked.

The forward motive force is transmitted across the filter and causes pressurization in the chamber filled with the compressible fluid. Some of the filtrate will move into this chamber as the compressible fluid shrinks under pressure. As soon as the forward motive force is removed (for example by stopping the inflow of unfiltered material or by turning off the pump) and the pressure in the upstream part of the filter is vented to atmosphere or any lower pressure level, the compressible fluid will expand in response to the drop in upstream pressure. This expansion will force the filtrate out of the chamber, reverse the flow of the solution across the filter and drain towards the same atmospheric or low pressure vent in the upstream side of the filter. This flow reversal will dislodge the particles in the upstream side of the filter and allow a recovery of filtration efficiency.

This invention is particularly suitable for hydrocarbon analyzers such as freeze point, cloud point and pour point analyzers. It is also useful for other types of hydrocarbon analyzers in which the measurement reliability is adversely affected by the presence of water and solid contaminants in the sample. Examples of these analyzers are those used in the measurement of vapor pressure, octane number and sulfur content in hydrocarbons.

A preferred apparatus for removing contaminants such as solids, free water and the like from a hydrocarbon sample stream is illustrated in the FIGURE. The normal direction of flow of sample is from the left of the diagram to the right as indicated by the arrows in the FIGURE. The references of downstream and upstream of a certain point are based on this flow direction. The apparatus preferably contains a hydrophobic membrane filter 1 which is installed inside a filter housing 2. In this housing, the membrane separates the inlet chamber 3 from the outlet chamber 4. The membrane will keep most of the water droplets and solids in the inlet chamber 3. There are two ports in the preferred inlet chamber; an entrance port 5 for the untreated liquid sample to come in and a bypass port 6 for the unfiltered liquid to leave the filter housing 2. The bypass port 6 is normally connected to an atmospheric drain tank (not shown). A pump 7 or other motive force device can be used to deliver untreated liquid to the filter housing 2. In a preferred embodiment, the liquid inside inlet chamber 3 flows along an inlet path (defined by a series of concentric grooves, not shown) while in intimate contact with the membrane 1. When a fresh sample is needed for analysis, valve 8, which is connected to the analyzer 9 and operated at a pressure lower than that inside the filter housing 2, will be opened. A portion of the liquid in the inlet chamber 3 will pass through the filter 1, leaving the solids and water droplets on the filter. The filtrate will first move into the outlet chamber 4 and continue on to the analyzer 9 after passing through exit port 12. The remaining liquid in the inlet chamber 3 flows rapidly along the concentric path and sweeps the water droplets together with some of the solids away from the filter membrane 1. The concentric flow path ensures a fast and uniform flow across the filter surface to facilitate the sweeping action. This "sweeping" liquid leaves the filter housing 2 through the bypass port 6, carrying with it the extra water and solids collected from the filter surface.

When sampling is complete, valve 8 will be closed. The analyzer 9 will then begin the measurement sequence. Once valve 8 is closed, all the incoming liquid will leave through the bypass port 6 after flowing through the concentric path. This will bring a fresh supply of sample to the conditioning unit while the analyzer 9 is analyzing the previous sample.

A conventional, prior art, design does employ the above described concentric grooves. However, with this design, we found that there were some fine solids that were trapped in the pores of the membrane 1. This fouling condition often applies to essentially all types of fuel samples, regardless of the bypass or "sweeping" flow rate. There were also instances when we found a film of very fine solids deposited on the membrane surface (not inside the pores) on the side facing the inlet chamber 3. As a result, the rate of filtration deteriorated over time.

A drop in filtration rate causes incomplete purging of the analyzer 9, which is undesirable because the analyzer would then contain a mixture of new and old sample. To compensate for the drop in filtration rate, we could increase the pressure in the inlet chamber while keeping the pressure in the analyzer constant. However, this technique has several drawbacks. First, one would need to design a control scheme which would monitor the filtration rate and automatically adjust the pressure in the inlet chamber. This type of control would tend to be complex and involve many components which are prone to failures. Also, the membrane has a maximum pressure at which it can keep the water droplets in the upstream side. A pressure higher than this maximum level may lead to water breaking through the membrane; as a result, hydrocarbon and water will be found downstream of the membrane. The presence of free water in the analyzer test cell will generally lead to false measurements.

Through a series of trials and errors, we invented an apparatus which is simple and yet effective in maintaining the filter efficiency. In the inventive apparatus, an anticlogging chamber 10 filled with gas (preferably air, nitrogen and other inert gases are also suitable), is installed as a side branch in the downstream side of the filter. Since gas has a much lower density than the hydrocarbon filtrate, it stays in the top part of the chamber 10. The preferred design shown in the FIGURE is "diaphragmless"; that is, there is no diaphragm in chamber 10. Possible modifications include the use of a diaphragm or piston to separate the compressible gas phase from the liquid filtrate phase. One may also separate the two phases by encapsulating the gas phase in a flexible covering which resembles a gas bladder. These are not preferred for reasons of cost and potential maintenance difficulties.

It should be noted that in the FIGURE, valve 8 is located between the anticlogging chamber 10 and the analyzer 9. This is preferred but not essential. This arrangement is applicable to analyzers with two major types of sample cell designs: open (to atmosphere) sample cell and completely enclosed flow through cell. If valve 8 were to be placed downstream of the analyzer 9, it would only work for analyzers with an enclosed flow through cell, but not the open cell design because pressurization in the anticlogging chamber 10 cannot be achieved in the latter case when valve 8 is closed while valve 11 is opened. On the other hand, putting valve 8 downstream of analyzer 9 that has an enclosed flow through cell design would have the advantage of a smaller dead volume. Also, bubbles that may created by the opening and closing actions of valve 8 will be flushed downstream of the analyzer by the flow of filtrate. These bubbles would not be able to get into the sample cell upstream and cause measurement interference.

As noted above, valve 8 is closed after every sampling. With valve 11 still open, the filter downstream pressure (P2) is lower than the upstream pressure (P1). The difference between P1 and P2 increases with the amount of solid blockage on the filter membrane 1. However, due to the presence of the forward motive force (preferably supplied by pump 7), both P1 and P2 could be significantly higher (5 to 6 psi or 35 to 41 kPa in our case) than that measured downstream of the bypass port (P3) which is normally kept at atmospheric pressure. Since P2 is higher than atmospheric pressure, the gas will be compressed and the bottom part of the chamber 10 will be filled with filtrate.

A backflush situation will develop as soon as valve 11 is closed, as follows: P1 quickly drops to about P3 because the positive motive force has been disconnected and there is little restriction between P1 and P3. P2 will also drop, but slower than P1 because it is separated from the drain (P3) by the membrane 1. The result is that the pressurized gas in the anticlogging chamber 10 expands and provides a backflush motive force across the membrane 1.

The amount of gas inside the anticlogging chamber 10 affects the size of the backflush force; therefore, it is important to maintain a relatively constant amount of gas inside this chamber 10. The amount of gas would decrease if part of this gas dissolves into the filtrate. On the other hand, the amount of gas would increase if the filtrate sample carries entrained gas bubbles from the sample source 14. A relatively constant amount of gas in the anticlogging chamber 10 can be maintained by installing a gas bleed valve 15 as shown. The gas bleed valve may be connected to the atmosphere or a reservoir (not shown) of inert gas kept at a fixed pressure. If the anticlogging chamber 10 is overfilled with gas, opening valve 15 will vent off the excess gas. If the anticlogging chamber 10 contains less gas than it should be through dissolution, opening valve 15 will allow fresh make-up gas to come in.

EXAMPLE

A device essentially as shown in the FIGURE was constructed using small diameter tubing materials. All the tubings 13 were ¼" diameter. The filter housing was disc-shaped, 3.5" diameter, 1.5" thick and contained the 3 ports 5, 6, 12 mentioned earlier. The pump 7 was an industrial positive displacement pump with a maximum flow capacity of 180 gallons per hour and maximum pressure of 50 psig. Valve 8 was a solenoid valve which is controlled for on and off operation by the microprocessor (not shown) located inside the analyzer 9. Valve 8 was opened for a fixed amount of time in every test run to deliver a sufficient quantity of filtrate to the analyzer. The weight of filtrate collected in each test was about 30 grams and was measured by a weighing scale with a design accuracy to 0.1 gram.

Table 1 presents the weight of filtrate per run for 40 test runs conducted sequentially, using the prior art setup which may be inferred in the FIGURE (i.e. the prior art device does not contain the anticlogging chamber 10). The first 29 runs were done using a light fuel with a freeze point of −19° C. A heavier fuel with a freeze point of −4° C. was used for the last 11 runs. The pressure P2 and temperature were kept essentially constant during the tests. These tests showed a gradual decline in the amount of filtrate obtained as the filter processed an increasing amount of material. Similar aging behavior was observed for both types of fuel. We have also experimented with approximately 20 other filters made by different manufacturers, numerous diesel and jet fuels, differential pressure (P2−P1) ranging from 1 psig to 50 psig, temperature ranging from 10° to 50° C. and different on/off timing for valve 8. The filter aging behavior was observed in all cases, although the rate of aging may vary. Without exception, a frequent replacement of filter was required, which was undesirable for industrial application.

Table 2 presents the results collected using the inventive device illustrated in the FIGURE, including the anticlogging chamber 10. In this setup, a valve 11 was added between the pump and the filter housing. Also, a cylindrical anticlogging chamber 10 having a height of 4.8" and an internal diameter of 0.25" was installed between the filter housing and valve 8. This anticlogging chamber 10 was filled with air under atmospheric pressure. Valve 8 was closed after sampling was complete for each run. While valve 8 was in the closed position, the chamber 10 was pressurized when valve 11 was opened, and some filtrate would occupy the lower part of the chamber 10. The chamber 10 would depressurize when valve 11 was closed. The filtrate would move out of the chamber, backflow across the filter 1 and leave the filter housing through the drain port 6. By opening and closing valve 11, a burst of backflush could be realized. In this set of experiments, valve 11 was opened and closed 7 times in each run to allow 7 backflush sequences. Some of the tests were also done without any backflush to illustrate the effects of backflush on filtration efficiency.

Table 2 illustrates the importance of backflush in maintaining a stable amount of filtrate in each test. The amount of filtrate per run dropped progressively whenever there was no backflush. When the backflush was activated, the amount of filtrate per run increased. With this filter membrane, the backflush technique was effective in improving the filtration efficiency even after a large number of runs conducted without backflush.

TABLE 1

Filtration efficiency with no backflush

| Run # | Amount of filtrate per run, grams | Freeze Point |
|---|---|---|
| 1 | 37.2 | Freeze point = −19° C. |
| 2 | 37.3 | Freeze point = −19° C. |
| 3 | 37.3 | Freeze point = −19° C. |
| 4 | 37.3 | Freeze point = −19° C. |
| 5 | 37.3 | Freeze point = −19° C. |
| 6 | 37.4 | Freeze point = −19° C. |
| 7 | 37.4 | Freeze point = −19° C. |
| 8 | 37.3 | Freeze point = −19° C. |
| 9 | 36.0 | Freeze point = −19° C. |
| 10 | 35.8 | Freeze point = −19° C. |
| 11 | 35.5 | Freeze point = −19° C. |
| 12 | 35.5 | Freeze point = −19° C. |
| 13 | 35.5 | Freeze point = −19° C. |
| 14 | 35.0 | Freeze point = −19° C. |
| 15 | 34.8 | Freeze point = −19° C. |
| 16 | 34.1 | Freeze point = −19° C. |
| 17 | 34.0 | Freeze point = −19° C. |
| 18 | 33.8 | Freeze point = −19° C. |
| 19 | 33.7 | Freeze point = −19° C. |
| 20 | 33.5 | Freeze point = −19° C. |
| 21 | 33.4 | Freeze point = −19° C. |
| 22 | 33.3 | Freeze point = −19° C. |
| 23 | 33.2 | Freeze point = −19° C. |
| 24 | 33.1 | Freeze point = −19° C. |
| 25 | 32.9 | Freeze point = −19° C. |
| 26 | 32.7 | Freeze point = −19° C. |
| 27 | 32.5 | Freeze point = −19° C. |
| 28 | 32.3 | Freeze point = −19° C. |
| 29 | 32.1 | Freeze point = −19° C. |
| 30 | 28.7 | Freeze point = −4° C. |
| 31 | 25.7 | Freeze point = −4° C. |
| 32 | 21.9 | Freeze point = −4° C. |
| 33 | 19.5 | Freeze point = −4° C. |
| 34 | 19.2 | Freeze point = −4° C. |
| 35 | 19.2 | Freeze point = −4° C. |
| 36 | 19.3 | Freeze point = −4° C. |
| 37 | 19.1 | Freeze point = −4° C. |
| 38 | 19.0 | Freeze point = −4° C. |
| 39 | 18.8 | Freeze point = −4° C. |
| 40 | 18.8 | Freeze point = −4° C. |

TABLE 2

Effect of backflush on filtration efficiency

| Run # | Amount of filtrate per run, grams | Number of backflush per run |
|---|---|---|
| 1 | 29.3 | 7 |
| 2 | 29.4 | 7 |
| 3 | 29.3 | 7 |
| 4 | 29.3 | 7 |
| 5 | 29.3 | 7 |
| 6 | 28.2 | 0 |
| 7 | 27.5 | 0 |
| 8 | 27.1 | 0 |
| 9 | 26.8 | 0 |
| 10 | 26.6 | 0 |
| 11 | 26.3 | 0 |
| 12 | 28.9 | 7 |
| 13 | 29.1 | 7 |
| 14 | 29.3 | 7 |
| 15 | 29.2 | 7 |
| 16 | 28.0 | 0 |
| 17 | 27.5 | 0 |
| 18 | 27.0 | 0 |
| 19 | 29.0 | 7 |
| 20 | 29.2 | 7 |
| 21 | 29.3 | 7 |
| 22 | 29.4 | 7 |
| 23 | 29.3 | 7 |
| 24 | 29.3 | 7 |
| 25 | 29.2 | 7 |
| 26 | 29.3 | 7 |
| 27 | 29.4 | 7 |
| 28 | 29.4 | 7 |
| 29 | 29.3 | 7 |
| 30 | 29.3 | 7 |
| 31 | 29.4 | 7 |
| 32 | 29.3 | 7 |
| 33 | 29.3 | 7 |
| 34 | 28.2 | 0 |
| 35 | 26.5 | 0 |
| 36 | 26.1 | 0 |
| 37 | 25.8 | 0 |
| 38 | 25.6 | 0 |
| 39 | 25.4 | 0 |
| 40 | 25.2 | 0 |
| 41 | 25.1 | 0 |
| 42 | 24.8 | 0 |
| 43 | 24.6 | 0 |
| 44 | 24.4 | 0 |
| 45 | 24.2 | 0 |
| 46 | 24.0 | 0 |
| 47 | 23.9 | 0 |
| 48 | 23.8 | 0 |
| 49 | 28.9 | 7 |
| 50 | 29.0 | 7 |

What is claimed is:

1. In combination a fluid hydrocarbon analyzer and a filter membrane located upstream of the analyzer, the improvement comprising a backflush system for said filter membrane, wherein the backflush system includes a backflush fluid comprised by a liquid being analyzed by the analyzer, an anticlogging chamber providing a backflush pressure due to energy stored from the pumping, by a pump, of the liquid being analyzed, and a compressible fluid which is operably associated with the liquid being analyzed, and wherein said compressible fluid is contained in said anticlogging chamber and said energy is stored in the compressible fluid.

2. The combination according to claim 1 wherein said anticlogging chamber is located downstream from the filter membrane.

3. The combination according to claim 2 wherein said anticlogging chamber may be isolated from said analyzer by closing a valve located downstream of said anticlogging chamber and upstream of said analyzer, and.

4. The combination according to claim 3 wherein said anticlogging chamber is diaphragmless.

5. The combination according to claim 4 wherein said anticlogging chamber is fitted with a bleed valve.

6. The combination according to claim 2 wherein said anticlogging chamber is diaphragmless.

7. The combination according to claim 6 wherein said anticlogging chamber is fitted with a bleed valve.

8. The combination according to claim 1 wherein said hydrocarbon analyzer is a freeze point analyzer.

9. The combination according to claim 1 wherein said hydrocarbon analyzer is a cloud point analyzer.

10. The combination according to claim 1 wherein said compressible fluid is in fluid communication with said liquid being analyzed.

11. A process for filtering a liquid sample to be supplied to an analyzer through a filter membrane and for backflushing the filter membrane comprising the steps of:
 (a) pumping the liquid sample through the filter membrane to the analyzer;
 (b) storing energy from the pumping of the sample in a compressible fluid contained in an anticlogging chamber downstream of said filter membrane, said anticlogging chamber being operably associated with said sample; and
 (c) stopping the pumping of the sample and lowering the pressure on the upstream side of said membrane thereby releasing the stored energy from said compressible fluid to force the liquid sample back through the filter membrane so as to backflush the filter membrane.

* * * * *